United States Patent [19]
Tsao

[11] 3,948,622
[45] Apr. 6, 1976

[54] SEPARATION OF AQUEOUS HYDROGEN CHLORIDE FROM GASEOUS CHLORINATED HYDROCARBONS

[75] Inventor: Utah Tsao, Jersey City, N.J.

[73] Assignee: The Lummus Company, Bloomfield, N.J.

[22] Filed: July 12, 1974

[21] Appl. No.: 488,247

[52] U.S. Cl........................................ 55/32; 55/71
[51] Int. Cl.²...................................... B01D 53/00
[58] Field of Search............... 55/71, 51, 46, 48, 82, 55/32

[56] References Cited
UNITED STATES PATENTS 3,315,440  4/1967  Alkemade.............................. 55/48
3,793,801  2/1974  Tsao..................................... 55/71

*Primary Examiner*—Charles N. Hart
*Assistant Examiner*—Robert H. Spitzer
*Attorney, Agent, or Firm*—Marn & Jangarathis

[57] ABSTRACT

A chlorinated hydrocarbon stream is cooled to condense water vapor and a major portion of the hydrogen chloride as aqueous hydrogen chloride. The uncondensed portion is further cooled by direct quenching with aqueous quench liquid to condense further water vapor, with the quench circuit being maintained on the alkaline side by the addition of base.

12 Claims, 1 Drawing Figure

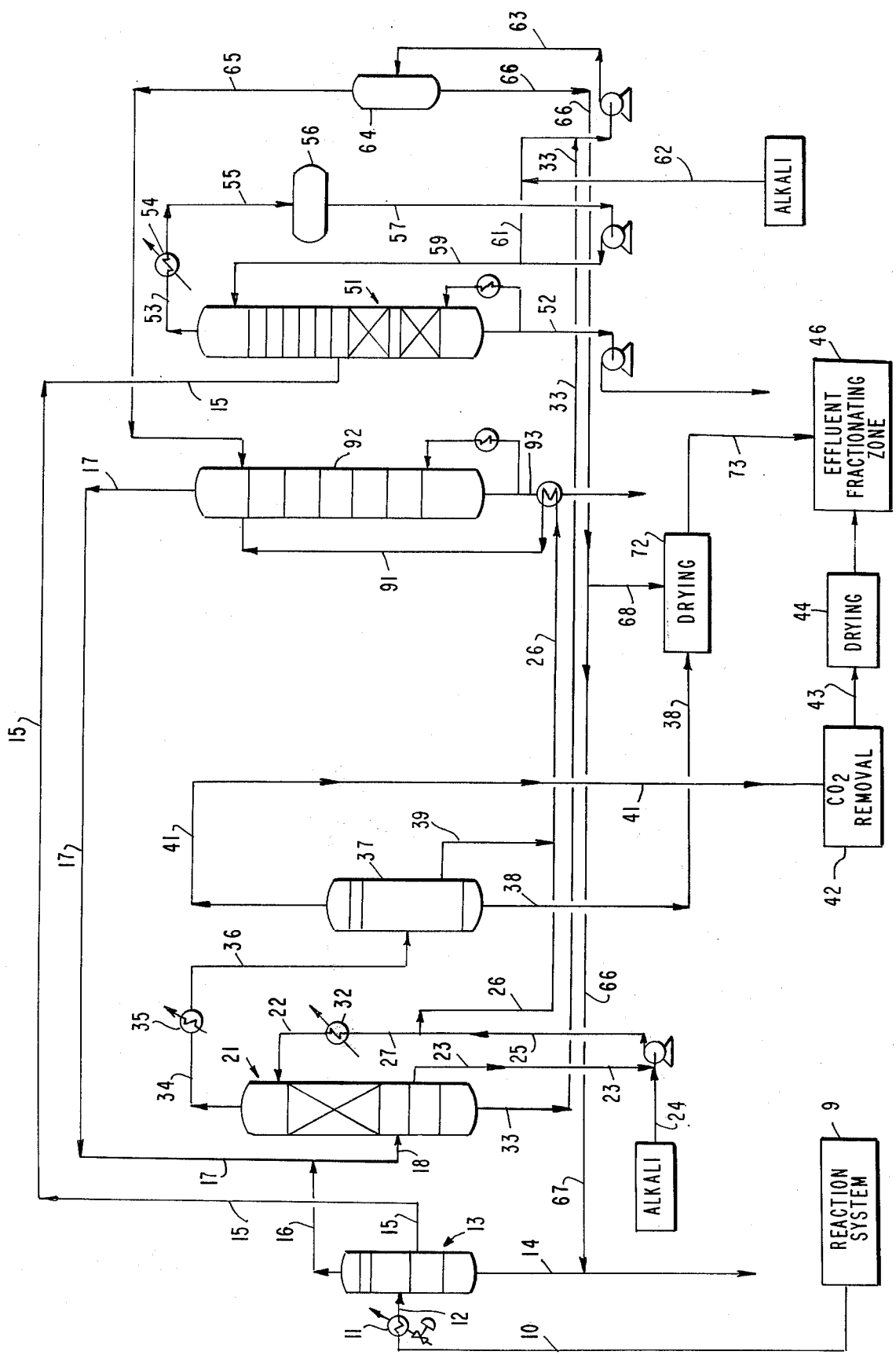

SEPARATION OF AQUEOUS HYDROGEN CHLORIDE FROM GASEOUS CHLORINATED HYDROCARBONS

This invention relates to the production of chlorinated hydrocarbons, and more particularly to a new and improved process for removing water from a chlorinated hydrocarbon effluent.

In the production of chlorinated hydrocarbons, in many cases, the chlorinated hydrocarbon effluent includes water vapor and hydrogen chloride. Accordingly, the separation and recovery section of a plant for producing chlorinated hydrocarbons generally includes a section for separating water vapor from the effluent. In such a section, as a result of the presence of hydrogen chloride, special materials must be employed in order to prevent corrosion.

An object of the present invention is to provide for improved recovery of chlorinated hydrocarbons.

Another object of the present invention is to provide a process for separating water from a chlorinated hydrocarbon effluent.

A further object of the present invention is to avoid corrosion problems in the separation of water from water-containing chlorinated hydrocarbon effluents.

These and other objects of the present invention should be apparent from reading the following description thereof.

In accordance with the present invention, a gaseous chlorinated hydrocarbon stream, containing chlorinated hydrocarbon, water vapor, hydrogen chloride gas and carbon dioxide is cooled to recover a major portion of the gaseous hydrogen chloride as a condensed aqueous hydrogen chloride solution. The uncondensed portion of the chlorinated hydrocarbon stream, containing equilibrium amounts of hydrogen chloride is then further cooled to condense remaining water vapor by direct contact with a circulating aqueous quench liquid, maintained on the alkaline side by the addition of alkali to the quench line whereby the hydrogen chloride contained in the water condensed from the gas is neutralized. In addition, any equilibrium amounts of uncondensed hydrogen chloride are neutralized by direct contact with the quench liquid, which contains carbonate and/or bicarbonate produced by reaction between alkali and carbon dioxide dissolved in the quench liquid (only limited quantities of carbon dioxide present in the gaseous stream are dissolved in the circulating quench liquid circuit). Thus, in accordance with the present invention, hydrogen chloride present in the gas stream introduced into the direct contact quench zone is effectively neutralized, in both the condensed liquid and gas, by the use of added alkali, whereby the quench circuit need not include specialized corrosion resistant equipment.

More particularly, a gaseous chlorinated hydrocarbon effluent, containing chlorinated hydrocarbons, and also generally containing unchlorinated hydrocarbons, water vapor, hydrogen chloride and carbon dioxide is cooled by indirect heat transfer to condense from the effluent an aqueous hydrogen chloride solution. As a result of such cooling, some chlorinated hydrocarbon is generally also condensed from the effluent. In general, the cooling is controlled to condense from the effluent, an aqueous hydrogen chloride solution having a hydrogen chloride concentration from about 5% to about 15%, and preferably from about 8% to about 12%, (all by weight). In order to effect the condensation of aqueous hydrogen chloride in the desired concentration, the chlorinated hydrocarbon effluent is generally cooled to a temperature from about 250°F to about 180°F, at a pressure from about 5 psig. to about 100 psig. It is to be understood that the hereinabove described temperatures and pressures are merely illustrative, and the scope of the invention is not to be limited thereby in that aqueous hydrogen chloride can be condensed at other temperatures and pressures. In general, at least 90%, preferably 95% or more, of the hydrogen chloride present in the effluent is separated in the initial cooling stage. As a result of equilibrium considerations, the chlorinated hydrocarbon effluent from the initial cooling stage includes hydrogen chloride.

The uncondensed portion of the effluent, which contains carbon dioxide and equilibrium amounts of hydrogen chloride (it is not possible to completely separate hydrogen chloride from the gas stream by condensation), is then further cooled by direct contact with an aqueous quench liquid, with such cooling resulting in the condensation of water vapor and additional chlorinated hydrocarbon. The quench cooling is effected to separate water vapor and further lower the temperature of the effluent for further processing thereof; i.e., the separation and recovery of various fractions. In general, the cooling is effected to a temperature from about 100°F to about 180°F, at a pressure from about 5 to about 100 psig.

In the direct contact quenching, the condensed water vapor is used as the direct contact quench liquid, and as a result of the presence of hydrogen chloride in the effluent introduced into the direct contact quench zone, the condensed water vapor would be acidic, thereby normally necessitating a quench circuit constructed of corrosion resistant materials, such as Monel alloys. In accordance with the present invention, alkali is added to the quench circuit to maintain the quench circuit on the alkaline side, thereby eliminating the necessity of using special corrosion resistant materials in the quench circuit pump and cooler. In addition, carbonate and/or bicarbonate is generated in the quench liquid by reaction between the alkali and dissolved carbon dioxide, and as a result, the contact between the quench liquid and gaseous chlorinated hydrocarbon neutralizes equilibrium amounts of hydrogen chloride which would normally be present in the gas, whereby the effluent withdrawn from the direct contact quench zone is essentially free of hydrogen chloride. The alkaline conditions are maintained in the quench circuit by the addition of a suitable base; preferably sodium or potassium hydroxide, which does not interfere with the operation of the system. The hydrogen chloride present in the water vapor condensed in the direct contact quench zone is neutralized by either the added base and/or the carbonate and/or bicarbonate produced by reaction between the base and dissolved carbon dioxide.

The uncondensed chlorinated hydrocarbon effluent may still contain some water vapor, which can be separated by further cooling of the effluent, either indirectly or directly, preferably indirectly.

In accordance with a preferred embodiment of the present invention, chlorinated hydrocarbons which are condensed from the chlorinated hydrocarbon effluent and which are to be introduced into the product fractionation system are introduced into a drying tower to strip water therefrom, and the overhead system of the drying tower is maintained on the alkaline side by introduction of alkali into the overhead, prior to the overhead condenser, thereby eliminating the necessity of using special materials of construction for the drying column overhead equipment. Liquid chlorinated hydrocarbon is recovered as bottoms from the drying tower for introduction into the product fractionation system.

In accordance with a further feature of the present invention, net water, condensed from the chlorinated hydrocarbon effluent, which is to be discarded from the system, is introduced into an oil stripping column to recover any entrained organic material. As should be apparent, the water recovered from the chlorinated hydrocarbon effluent is discarded as an aqueous salt solution, with the salt being formed by reaction of hydrogen chloride with the added alkali. As hereinabove described, in general, the water is discarded as an aqueous brine solution.

The chlorinated hydrocarbon effluent which is treated in accordance with the present invention may be produced by any one of a wide variety of chlorination and/or oxychlorination processes. The net feed to such a process can be a hydrocarbon and/or a partially chlorinated hydrocarbon. As representative examples, there may be mentioned: aromatic hydrocarbons, such as benzene; aliphatic hydrocarbons (saturated or olefinically unsaturated), preferably a $C_1$ to $C_4$ aliphatic hydrocarbon; or partially chlorinated derivatives of such aromatic or aliphatic hydrocarbons. The most preferred feeds are ethane, ethylene, methane and partially chlorinated derivatives thereof.

The present invention is particularly applicable to processes for producing chlorinated $C_2$ hydrocarbons and chlorinated methanes by the use of molten salts, wherein the feed is contacted with hydrogen chloride and/or chlorine and a molten salt containing a multivalent metal chloride in its higher and lower valence state and the oxychloride of the metal (preferably copper chlorides and oxychloride). Such a process for producing chloromethanes is described in U.S. Application Ser. Nos. 299,114 and 299,848, and such a process for vinyl chloride is described, for example, in U.S. Application Ser. No. 153,374, all of which are hereby incorporated by reference.

The teachings of the present invention are also applicable to oxychlorination processes in which a hydrocarbon or partially chlorinated hydrocarbon is directly contacted with oxygen and hydrogen chloride, as known in the art.

Referring now to the drawing, a chlorinated hydrocarbon effluent produced in a reaction system 9 is withdrawn through line 10. The effluent in line 10 generally includes chlorinated hydrocarbon, hydrocarbon, water vapor, hydrogen chloride, carbon dioxide and non-condensibles such as nitrogen. Thus, for example, in the production of vinyl chloride, by the use of molten salts, the effluent would include, $C_2$ hydrocarbon(s), chlorinated $C_2$ hydrocarbons, water vapor, hydrogen chloride, etc. and in the production of chloromethanes, the effluent would include methane, chloromethanes, water vapor, hydrogen chloride, etc.

The effluent in line 10 is passed through condenser 11 where the effluent is indirectly cooled to a temperature, as hereinabove described, which condenses an aqueous hydrogen chloride solution, and in addition, some chlorinated hydrocarbon. The cooled effluent, in line 12, is introduced into a separator 13 wherein the condensed portion is separated into an organic phase comprising chlorinated hydrocarbon and an aqueous phase of dilute hydrochloric acid. The condensed organic phase is withdrawn from separator 13 through line 14 and may be employed as a quench liquid in the reaction system 9.

The condensed aqueous phase is withdrawn from separator 13 through line 15 and is introduced into a stripper, as hereinafter described, to produce a more concentrated hydrochloric acid.

The uncondensed portion of the chlorinated hydrocarbon effluent, containing hydrocarbon, chlorinated hydrocarbon, water vapor, hydrogen chloride, carbon dioxide, etc., is withdrawn from separator 13 through line 16, combined with organics, in line 17, recovered from an oil stripper, as hereinafter described, and the combined stream in line 18 is introduced into a direct contact quench vessel 21.

In quench vessel 21, the gaseous effluent is directly contacted with an aqueous quench liquid, introduced through line 22, to indirectly cool the effluent and condense additional water vapor therefrom. In addition, some chlorinated hydrocarbon is also condensed from the effluent. The condensed portion forms an aqueous phase and an organic phase in the bottom of the quench tower 21.

The condensed aqueous phase is withdrawn from quench vessel 21 through line 23 and combined with alkali, such as sodium hydroxide, in line 24. The amount of alkali added through line 24 is controlled to maintain alkaline conditions in the aqueous phase to be used as quench liquid in quench tower 21.

A portion of the alkaline aqueous phase, in line 25, is passed through line 26 to an oil stripper, as hereinafter described, as net aqueous make, for purging from the system. As should be apparent, the aqueous phase is discarded from the system as an aqueous salt solution produced by reaction of hydrogen chloride with the added alkali. The remainder of the aqueous phase, in line 27, is passed through quench cooler 32 wherein the aqueous quench liquid is cooled to a temperature suitable for providing the cooling requirements for quench tower 21. The cooled quench liquid from cooler 32 is introduced into the quench tower 21 through line 22. The cooled quench liquid which is introduced into tower 21, includes carbonate and/or bicarbonate, which neutralizes any hydrogen chloride remaining in the chlorinated effluent whereby the effluent withdrawn through line 34 is free of hydrogen chloride.

The organic phase is withdrawn from quench tower 21 through line 33 and, as hereinafter described, is either employed as quench liquid and/or dried for eventual introduction into the effluent fractionation system.

The uncondensed portion of the chlorinated hydrocarbon effluent is withdrawn from quench tower 21 through line 34, indirectly cooled in condenser 35 to condense any remaining water vapor. The cooled effluent, in line 36, is introduced into a knock-out drum 37 to separate condensed water, with the condensed water being withdrawn from drum 37 through line 39, and the chlorinated hydrocarbon through line 38 for further treatment, as hereinafter described.

The uncondensed portion of the chlorinated hydrocarbon effluent, containing carbon dioxide, and essentially free of water vapor, is withdrawn from drum 37 through line 41, compressed and introduced into a carbon dioxide removal system, of a type known in the art, and schematically indicated as 42. After removal of carbon dioxide, the gaseous chlorinated hydrocarbon effluent, in line 43 is passed through a drying zone, schematically indicated as 44, and an effluent fractionation zone, schematically indicated as 46, to recover the various components thereof.

The aqueous phase in line 15, comprised of dilute hydrochloric acid, is introduced into an acid concentration column 51 designed and operated to produce a more concentrated hydrochloric acid, generally having a concentration from about 15 to about 20%. The tower 51 is generally operated at an overhead temperature from about 215°F to about 240°F, a bottoms temperature from about 230°F to about 255°F and a pressure from about 1 psig. to about 10 psig. A bottoms of concentrated hydrochloric acid is withdrawn through line 52.

Overhead withdrawn from column 51 through line 53 is condensed in condenser 54 and introduced through line 55 into a reflux drum 56. A first portion of the condensed overhead withdrawn from reflux drum 56 through line 57 is passed through line 59 to meet the reflux requirements of tower 51. A second portion of the condensed overhead in line 61 is combined with alkali in line 62, preferably sodium hydroxide, to maintain alkaline conditions, and further combined with the organic phase withdrawn from tower 21 through line 33. The organic phase functions as a wash liquid to wash organics from the aqueous condensed overhead from column 51 and thereby reduce the load on an oil stripper. The combined stream, in line 63, is introduced into a separator 64 to separate aqueous and organic phases. The aqueous phase is withdrawn from separator 64 through line 65 for treatment in an oil stripper, as hereinafter described, prior to being discarded from the system.

The organic phase is withdrawn from separator 64 through line 66 and all or a portion thereof may be passed through line 67 for use as a quench liquid.

Alternatively all or a portion of the organic phase in line 66 may be passed through line 68, and introduced into drying zone 72 along with the condensed chlorinated hydrocarbon in line 38 to effect drying thereof prior to being introduced through line 73 into the effluent fractionation system 46.

The water vapor condensed in quench tower 21 not used for meeting quench requirements is passed through line 26, combined with condensed water in line 39, and introduced into a stripping column 92 to strip organic material therefrom, prior to discarding the aqueous phase. The water phase, from acid concentrator 51, in line 65, is also introduced into stripping column 92 for the same purpose. The column 92 is generally operated at an overhead temperature from about 235°F to about 305°F, a bottoms temperature from about 240°F to about 310°F and a pressure from about 10 to about 60 psig.

An organic overhead is recovered from column 92 through line 17 for introduction into the quench column 21, as hereinabove described. An aqueous salt solution, which is a brine solution when sodium hydroxide is used as alkali, is withdrawn, as bottoms, from column 92, through line 93, for discarding from the system.

As should be apparent from the hereinabove described embodiment, in accordance with the present invention, water vapor and hydrogen chloride are effectively separated from a chlorination effluent. Furthermore, by maintaining alkaline conditions in the various aqueous liquid circuits, problems associated with corrosive hydrogen chloride are eliminated, without the necessity of using expensive materials of construction and/or large amounts of alkali.

The invention will be further described with respect to the following example, but the scope of the invention is not to be limited thereby.

EXAMPLE

The following is illustrative of the quenching operation for a chlorination effluent containing $C_2$ hydrocarbons and chlorinated $C_2$ hydrocarbons.

The effluent is initially cooled to a temperature of about 190°F at a pressure of about 40 psig, and then cooled in tower 21 to a temperature of about 110°F at a pressure of about 40 psig. The various streams are tabulated in the following Table.

MATERIAL BALANCE IN 1,000 LB/HR

| Stream No. Components | 12 | 14 | 15 | 16 | 17 | 18 | 23 | 24 | 25 | 26 | 33 | 34 |
|---|---|---|---|---|---|---|---|---|---|---|---|---|
| Non-condensibles | 3.70 | — | — | 3.70 | — | 3.70 | — | — | — | — | — | 3.70 |
| $CO_2$ | 4.50 | 0.11 | — | 4.39 | — | 4.39 | 0.10 | — | — | — | 0.06 | 4.23 |
| Ethylene | 18.50 | 0.21 | — | 18.29 | — | 18.29 | — | — | — | — | 0.10 | 18.19 |
| Ethane | 35.50 | 0.39 | — | 35.11 | — | 35.11 | — | — | — | — | 0.22 | 34.89 |
| Chlorinated Hydrocarbons | 899.50 | 531.99 | 0.11 | 367.40 | 0.33 | 367.73 | 8.40 | — | 8.40 | 0.21 | 210.00 | 157.52 |
| HCl | 2.00 | 0.26 | 1.65 | 0.09 | — | 0.09 | — | — | — | — | — | — |
| Water | 36.30 | 2.14 | 14.40 | 19.76 | 3.13 | 22.89 | 838.84 | 0.76 | 839.60 | 20.99 | 0.91 | 1.77 |
| NaOH | — | — | — | — | — | — | — | 0.19 | — | — | — | — |
| NaOH | — | — | — | — | — | — | 5.60 | — | 5.60 | 0.14 | — | — |
| $NaHCO_3$ | — | — | — | — | — | — | 8.00 | — | 7.79 | 0.19 | — | — |
| $Na_2CO_3$ | — | — | — | — | — | — | — | — | 0.50 | 0.01 | — | — |
| TOTAL | 1000.00 | 535.10 | 16.16 | 448.74 | 3.46 | 452.20 | 860.94 | 0.95 | 861.89 | 21.44 | 211.29 | 220.30 |

The present invention is particularly advantageous in that a chlorinated hydrocarbon effluent, containing water vapor, hydrogen chloride and carbon dioxide is treated to separate water vapor and hydrogen chloride in a system employing direct contact quench cooling, without the necessity of using special materials in the quench cooling circuit and without requiring the use of large amounts of base. In accordance with the present invention, by adding the alkali to the quench circuit, all of the carbon dioxide introduced into the quench zone need not be neutralized in order to protect the quench circuit from corrosive hydrogen chloride.

Numerous modifications and variations of the present invention are possible in light of the above teachings and, therefore, within the scope of the appended claims the invention may be practiced otherwise than as particularly described.

What is claimed is:

1. A process for treating a gaseous chlorinated hydrocarbon effluent containing hydrogen chloride, water vapor and carbon dioxide, comprising:
   a. cooling the gaseous chlorinated hydrocarbon effluent to condense aqueous hydrogen chloride containing the major portion of the hydrogen chloride present in said gaseous chlorinated hydrocarbon effluent;
   b. introducing uncondensed effluent from step (a) into a direct contact quench zone;
   c. contacting the uncondensed chlorinated hydrocarbon effluent with quench liquid to cool the effluent and condense further water vapor;
   d. withdrawing condensed water vapor from the quench zone and adding base to the withdrawn condensed water vapor to maintain the condensed water vapor on the alkaline side;
   e. cooling a portion of the condensed water vapor from step (d); and
   f. employing the cooled portion of the condensed water vapor from step (e) as the quench liquid in the quench zone.

2. The process of claim 1 wherein the cooling in step (a) is effected to produce aqueous hydrogen chloride having a hydrogen chloride concentration from 5% to 15%, by weight, said uncondensed effluent containing equilibrium amounts of hydrogen chloride.

3. The process of claim 2 wherein the cooling in step (a) is effected to a temperature from 180°F to 250°F, at a pressure from 5 to 100 psig.

4. The process of claim 3 wherein the uncondensed chlorinated hydrocarbon effluent is cooled in step (c) to a temperature from 100°F to 180°F at a pressure from 5 psig. to 100 psig. and the uncondensed chlorinated hydrocarbon effluent withdrawn from the direct contact quench zone is free of hydrogen chloride.

5. The process of claim 4 wherein the base added in step (d) is sodium hydroxide.

6. The process of claim 5 wherein the chlorinated hydrocarbon effluent contains $C_2$ hydrocarbon and chlorinated $C_2$ hydrocarbon.

7. The process of claim 5 wherein the chlorinated hydrocarbon effluent contains methane and chloromethanes.

8. The process of claim 5 and further comprising:
   introducing a further portion of the condensed water vapor from step (d), containing chlorinated hydrocarbon into a stripping zone;
   stripping chlorinated hydrocarbon from the further portion of condensed water vapor; and
   discarding the stripped condensed water vapor.

9. The process of claim 8 and further comprising:
   introducing condensed aqueous hydrogen chloride from step (a) into a hydrogen chloride concentration zone to concentrate the aqueous hydrogen chloride by stripping water therefrom;
   withdrawing stripped water, containing chlorinated hydrocarbon from said hydrogen chloride concentration zone; and
   introducing the stripped water containing chlorinated hydrocarbon into said stripping zone.

10. The process of claim 9 wherein chlorinated hydrocarbon recovered in said stripping zone is introduced into the direct contact quench zone.

11. The process of claim 10 wherein the cooling of step (c) effects condensation of chlorinated hydrocarbon and chlorinated hydrocarbon condensed in step (c) is employed to wash a portion of the chlorinated hydrocarbon from the stripped water from the hydrogen chloride concentration zone, prior to introduction of the stripped water into the stripping zone.

12. The process of claim 11 wherein alkali is added to the stripped water prior to introduction thereof into the stripping zone.

* * * * *